US006984492B2

(12) United States Patent
Betz et al.

(10) Patent No.: US 6,984,492 B2
(45) Date of Patent: Jan. 10, 2006

(54) METHODS AND COMPOSITIONS FOR TREATING HERPES INFECTIONS (75) Inventors: Ulrich Betz, Wuppertal (DE); Klaus-Peter Radtke, Apex, NC (US)

(73) Assignee: Talecris Biotherapeutics, Inc., Research Triangle Park, NC (US)

( * ) Notice: Subject to any disclaimer, the term of this patent is extended or adjusted under 35 U.S.C. 154(b) by 228 days.

(21) Appl. No.: 10/656,781

(22) Filed: Sep. 5, 2003

(65) Prior Publication Data

US 2005/0053605 A1 Mar. 10, 2005

(51) Int. Cl.
*C12Q 1/68* (2006.01)
(52) U.S. Cl. .............................. 435/6; 435/7.1; 435/345
(58) Field of Classification Search ................ 435/345, 435/6, 7.1
See application file for complete search history.

(56) References Cited

U.S. PATENT DOCUMENTS

| 5,505,945 | A | 4/1996 | Gristina et al. | .......... | 424/164.1 |
| 5,530,102 | A | 6/1996 | Gristina et al. | .......... | 530/391.1 |
| 5,681,565 | A | 10/1997 | Gristina et al. | .......... | 424/164.1 |
| 5,707,627 | A | 1/1998 | Gristina et al. | .......... | 424/164.1 |
| 5,718,899 | A | 2/1998 | Gristina et al. | .......... | 424/164.1 |
| 5,817,312 | A | 10/1998 | Gristina et al. | .......... | 424/164.1 |

FOREIGN PATENT DOCUMENTS

RU  2051 054 C1  12/1995

OTHER PUBLICATIONS

Rector et al, Infection and Immunity, Oct. 1982, vol. 38, No. 1, pp. 168-174.*
Dix et al, Infection And Immunity, Oct. 1981, vol. 34, No. 1, pp. 192-199.*
Boggess, K.A., et al., "Herpes simplex virus type 2 detection by culture and polymerase chain reaction and relationship to genital symptoms and cervical antibody status during the third trimester of pregnancy," *Am. J. Obstet. Gynecol.*, 176(2): 443-451 (1997).

Corbino, N., et al., "The role of anti-herpes specific serum IgA levels as a marker in cervical oncogenesis," *Eur. J. Gynaec. Oncol.*, 10(2): 103-108 (1989).
Habeeb, A.F.S.A., and R.D. Francis, "Preparation of human immunoglobulin free of plasmin and anticomplement activities," *Vox Sang.* 32(3): 143-158 (1977).
Leibl, H., et al., Method for the isolation of biologically active monomeric immunoglobulin A from a plasma fraction, *Journal of Chromatography B.*, 678(2):173-180 (1996).
European Patent Office Partial International Search Report (PCT/US2004/028559, dated Dec. 9, 2004).
Elrich, K.S., et al., "Prevention and Treatment of Experimental Herpes Simplex Virus Encephalitis with Human Immune Serum Globulin," *Antimicrobial Agents and Chemotherapy*, 31(7): 1006-1009 (1987).
Epstein, S.P, et al., "Efficacy of Polyclonal Antibodies for Treatment of Ocular Herpes Simplex Infection," *Cornea*, 20(5): 495-500 (2001).
LeBlanc, R.A., et al., "Treatment of HSV-1 Infection with Immunoglobulin or Acyclovir: Comparison of Their Effects on Viral Spread, Latency, and Reactivation," *Virology*, 262 (1): 230-236 (1999).
Raizman, M.B, and C.S. Foster, "Passive transfer of anti-HSV-1 IgG protects against stromal keratitis in mice," *Current Eye Research*, 7(8): 823-829 (1988).
Ritchie, M.H., et al., "Passive Transfer of Anti-Herpes Simplex Virus Type 2 Monoclonal and Polyclonal Antibodies Protect Against Herpes Simplex Virus Type 1-Induced but Not Herpes Simplex Virus Type 2-Induced Stromal Keratitis," *Investigative Opthalmology & Visual Science*, 34(8): 2460-2468 (1993).

* cited by examiner

*Primary Examiner*—Ali R. Salimi
(74) *Attorney, Agent, or Firm*—Womble Carlyle Sandridge & Rice, PLLC (57) ABSTRACT

A method of treatment or prophylaxis of herpes infections and associated disease states by administration of compositions comprising immunoglobulins. Methods comprising intravenous and topical administration of immunoglobulins are provided.

6 Claims, 4 Drawing Sheets

METHODS AND COMPOSITIONS FOR TREATING HERPES INFECTIONS

FIELD OF THE INVENTION

The invention relates to the administration of compositions comprising immunoglobulins for the treatment and/or prophylaxis of herpes infections and associated disease states. The invention provides aspects relating to intravenous and topical administration of the compositions of the invention.

BACKGROUND OF THE INVENTION

Herpesviruses evolved over millions of years and are highly disseminated in nature. Members of the family were identified in humans, non-human primates and most other mammals and vertebrates. Herpesviruses are enveloped double stranded DNA viruses, infecting cells that carry negatively charged structures such as heparin sulfate and or glycosaminoglycans, in addition to a herpes viral entry mediator, on their surface. A characteristic feature of these viruses is their ability to remain latent in their host for life after primary infection and to reactivate more or less frequently from a pool of latent infected cells upon diverse internal and external stimuli.

Herpes simplex virus (HSV) can cause severe life-threatening infections in immunocompromised patients and in the neonate, while exhibiting a self-limiting disease in an immunocompetent host. HSV is the major cause of sporadic acute encephalitis in the western world, with a mortality exceeding 70% when untreated. Neonatal HSV infection has a poor prognosis despite antiviral therapy (e.g., acyclovir). Twenty-five percent of infants who contract herpes at delivery will develop a disseminated herpetic infection and suffer a 40% mortality despite antiviral therapy. Accordingly, new ways to treat life-threatening HSV disease are urgently needed.

Even in immunocompetent humans, HSV can cause corneal infection leading to permanent scarring, loss of vision, and blindness. Epithelial keratitis is the most common presentation of ocular infection by HSV. Despite the availability of antivirals and steroids to suppress inflammation associated with acute herpetic disease, chronic HSV continues to cause significant ocular morbidity. Accordingly, new ways to treat HSV ocular disease are urgently needed.

SUMMARY OF THE INVENTION

Accordingly, in one aspect, the invention relates to a method of treatment or prophylaxis of herpes simplex virus (HSV) infections in mammals by administering intravenously to the mammal an effective amount of a composition comprising immunoglobulin A (IgA) prepared from pooled human plasma. The mammal can be a neonatal human. The mammal can be immunocompromised and/or suffer from a herpetic disease. The herpetic disease can be encephalitis, pneumonia, hepatitis, herpes ocularis, chickenpox, shingles, zoster oticus, zoster varicellosus, keratitis, herpes digitalis, herpes facialis, herpes genitalis, herpes gladiatorum, or herpes stomatitis. More than one of any of the foregoing can characterize the herpetic disease afflicting the mammal.

In some embodiments, the IgA comprises at least from about 35% to about 55% of any immunoglobulins present in the composition (the minimum amount of IgA as a percentage of the total immunoglobulin present can be from about 35% to about 55%). In other embodiments, the IgA can comprise at least from about 60% to about 80% of any immunoglobulins present in the composition.

In another aspect, the invention relates to a method of treatment or prophylaxis of herpes simplex virus (HSV) infections in mammals by administering intravenously to the mammal an effective amount of a composition comprising monomeric IgA, dimeric IgA, and IgG prepared from pooled human plasma, wherein monomeric and dimeric IgA comprise at least from about 35% to about 55% of the total immunoglobulins present in the composition. In some embodiments, monomeric and dimeric IgA comprise at least from about 60% to about 80% of the total immunoglobulins present in the composition. In other embodiments, monomeric and dimeric IgA comprise at least from about 70% to about 95% of the total immunoglobulins present in the composition. In still other embodiments, the monomeric and dimeric IgA comprise at least about 60%, at least about 80%, or at least about 90% of the total immunoglobulins present in the composition.

In another aspect, the invention relates to a method of treatment or prophylaxis of herpetic disease in mammals by administering topically to the mammal an effective amount of a composition comprising immunoglobulin G (IgG) prepared from pooled human plasma. The herpetic disease can be chickenpox, shingles, zoster oticus, zoster varicellosus, keratitis, herpes digitalis, herpes facialis, herpes genitalis, herpes gladiatorum, or herpes stomatitis.

In another aspect, the invention relates to a method of treatment or prophylaxis of ocular herpetic disease in mammals by administering topically to a mammal an effective amount of a composition comprising immunoglobulin G (IgG) prepared from pooled human plasma. The herpetic disease can be keratitis.

In still another aspect, the method of treatment or prophylaxis of ocular herpetic disease in mammals by administering a suspension comprising an effective amount of immunoglobulin G (IgG) prepared from pooled human plasma directly to an infected eye of a mammal.

BRIEF DESCRIPTION OF THE FIGURES

In FIG. 3A, the "boxes" surrounding particular bands, from right to left, represent intact IgA, intact IgG, $\mu$ h-chain of IgM, and intact IgA. "IgA Bayer" is IgA prepared according to the method of the present invention.

In FIG. 4A, the boxes surrounding particular bands, from right to left, represent $\alpha$ h-chain (60 kDa), $\gamma$ h-chain (55 kDa), $\mu$ h-chain (70 kDa), and $\alpha$ h-chain (60 kDa).

DETAILED DESCRIPTION OF THE INVENTION

The present invention provides a new method for treatment and prevention of disseminated HSV disease by intravenous administration of monomeric IgA (mIgA) and/or dimeric IgA (dIgA) fractions of human serum. In contrast to the results achieved by the present invention, it was previously suggested that HSV protection cannot be achieved by IgG-depleted serum (see Raizman, M. B. and C. S. Foster, Curr. Eye. Res. 7:823–829 (1988)). Accordingly, the IgA compositions of the present invention have not been used previously for treatment of HSV infections.

IgA fractions constitute an enormous commercial value because they are typically discarded as by-products of IgG purification from human serum. Further, use of IgA over other immunoglobulins is advantageous because IgA does not activate the classic pathway of the complement system and only slowly activates the alternative complement pathway. Consequently, IgA does not promote inflammation.

The present invention also provides a new method for treatment and prevention of HSV disease by using purified human IgG from pooled human plasma via topical treatment. This aspect of the invention has the additional advantage that no injection of immunoglobulin is necessary. Patients can treat themselves with topical IgG in an ophthalmic formulation. IgG from pooled human plasma is suitable for this purpose without a need for screening of blood donors based on their HSV-neutralizing antibody level. With respect to treatment or prophylaxis of ocular herpetic disease, the compositions of the invention can be administered directly onto the cornea of the infected eye. However, topical administration according the invention is not limited to ocular disease. The IgG compositions of the invention can be administered topically to other manifestations of HSV-related disease.

The compounds as herein provided can be used for treatment and prophylaxis of diseases caused by herpes simplex viruses. The following indications are listed as illustrative examples and are not intended to limit the scope of the invention: 1) treatment and/or prophylaxis of herpes simplex virus infections in patients with disease symptoms such as herpes ocularis, labialis, genitalis, keratitis, encephalitis, pneumonia, hepatitis, etc., caused by herpes viruses; 2) treatment and/or prophylaxis of herpes simplex virus infections in immunocompromised patients (e.g., AIDS patients, transplant recipients, cancer patients, patients with genetically based immunodeficiency); 3) treatment and/or prophylaxis of herpes simplex virus infections in newborns, babies, infants and children; 4) treatment and/or prophylaxis for herpes simplex virus positive patients for maintenance or suppression therapy of recurrent herpes disease; and 5) treatment and/or prophylaxis herpes simplex virus disease in the elderly.

As used herein, the term "effective amount" means an amount sufficient to produce a therapeutic result. Generally, the therapeutic result is an objective or subjective improvement of a disease or condition, achieved by inducing or enhancing a physiological process, blocking or inhibiting a physiological process, or in general terms performing a biological function that helps in or contributes to the elimination or abatement of the disease or condition.

Unless otherwise indicated, the term "purified" means that a substance has been removed from its original environment, such that the relative abundance of the substance has been increased in the context of other components of the composition. Alternatively or additionally, the term can be used solely to indicate that at least one particular contaminant has been reduced or removed from the composition comprising the substance.

The term "pharmaceutically acceptable carrier" refers to any compatible non-toxic material suited for mixing with the active compounds of the present invention.

The phrase "prepared from pooled plasma" means that the immunoglobulin preparations modified by this phrase were recovered from pooled plasma originating from blood donors. The compositions of the invention do not require that such donors be screened to determine their levels of HSV-neutralizing antibody.

The present invention relates to compositions and their use in medical therapy for the treatment and/or prophylaxis of herpes viral infections including herpes simplex viruses type-1 and type-2 (HSV-1 and HSV-2), varicella zoster virus (VZV), cytomegalovirus (CMV), and Epstein-Barr virus (EBV). The present invention can be used in the treatment and/or prophylaxis of recurrent herpes simplex type 1 or 2, herpes zoster (chicken pox, shingles), zoster otisis, zoster varicellosis, genital warts, or herpes keratitis, herpes digitalis, herpes facialis, herpes genitalis, herpes gladiatorum, and herpes stomatitis. Such diseases and conditions are well known and readily diagnosed by physicians of ordinary skill.

Intravenously administered compositions of the invention can be used for the treatment and/or prophylaxis of disseminated infections, thereby preventing herpes-related disease such as herpetic encephalitis. Such compositions can be used for the treatment and/or prophylaxis of neonatal infections, thereby treating or preventing disseminated infections that currently generate a high mortality rate. Immunocompromised individuals, including neonates and the elderly, are particularly susceptible to such diseases and benefit from administration of the compositions of the invention.

Although the intravenous administration of compositions comprising IgA can provide particular benefits to subjects suffering from disseminated herpes infections, e.g., infections giving rise to encephalitis, it will be recognized that such treatment can also benefit those suffering from any of the usual manifestations of herpes infection. Similarly, although topical administration of the immunoglobulin compositions of the invention can directly benefit subjects suffering from topical manifestations of herpes infection, e.g., keratitis, the administration of such compositions can provide benefits to those suffering from the effects of disseminated herpes infection.

The compositions of the invention can be prepared by employing conventional techniques to combine the compounds of the invention with pharmaceutically acceptable carriers, and optionally, with pharmaceutically acceptable excipients employing standard and conventional techniques. The topical formulations can also include a material that enhances absorption or penetration of the compounds of formula II or III through the skin or other affected areas.

The quantity of active component, e.g. an immunoglobulin preparation of the invention, in a pharmaceutical composition can be varied or adjusted widely depending upon the requirements of the patient, the severity of viral infections, the potency of the particular compound being used, the particular formulation and the desired concentration. Generally, the quantity of active component will range from about 0.05% to about 25% by weight of the composition, from about 0.1% to about 10% by weight, or from about 3% to about 16% of the composition.

For infections of the external tissues, e.g., mouth, eyes and skin, the formulations can be applied as a topical ointment or cream containing the active ingredient in an amount of, for example, about 0.05 to about 25% by weight of composition, or about 0.1 to about 10% w/w. When formulated in an ointment, the active ingredients can be employed with either a paraffinic or a water-miscible ointment base. Alternatively, the active ingredients can be formulated in a cream with an oil-in-water cream base.

Formulations suitable for topical administration in the eyes include eye drops wherein a composition of the invention is dissolved or suspended in a suitable carrier, especially an aqueous solvent. The active ingredient can be present in such formulations in a concentration of about 0.05 to about 25%, advantageously about 0.5 to about 10%.

Formulations suitable for topical administration in the mouth include lozenges comprising a composition of the invention in a flavored bases, e.g., sucrose and acacia or tragacanth; pastilles comprising the active ingredient in an inert base, e.g., gelatin and glycerin, or sucrose and acacia; and mouth-washes comprising the active ingredient in a suitable liquid carrier.

The ophthalmic dosage forms include solutions and suspensions prepared for use as eye drops to provide immediate therapeutic levels of the compositions of the invention and ophthalmic ointments designed to provide slower release rates or for use at bedtime.

The eye drop dosage form of the invention will optionally include one or more suitable and pharmaceutically acceptable inactive excipients, including, but not limited to: preservatives from a group including, but not limited to, benzalkonium chloride, methylparaben, edetate disodium, thimersol, and chlorbutanol; buffers from a group including, but not limited to, sodium citrate, sodium acetate, citric acid, and sodium lactate; vehicles from a group including, but not limited to, polyvinyl alcohol, hydroxy methylcellulose, cetyl alcohol, carboxymethylcellulose, and hydroxypropylenemethyl cellulose; pH adjusters from a group including, but not limited to, sulfuric acid, hydrochloric acid, sodium hydroxide, monosodium or disodium phosphate; purified water USP; poloxamer 407 or 188, polysorbate 80; polyoxyethylene polyoxypropylene compound; and mineral oil USP. The foregoing inactive excipients can serve a variety of functions as carriers, vehicles, diluents, binders, preservatives, buffers, pH adjusters, emulsifiers, and other formulating aids.

An ophthalmic ointment dosage form for prolonged delivery of the formulation or for use during sleep will optionally include one or more pharmaceutically acceptable inactive excipients, including, but not limited to: chlorbutanol, polyethylene mineral oil gel, white petrolatum USP, mineral oil USP, petrolatum and lanolin alcohol, purified water USP, polyvinyl alcohol gel and similar products. The above excipients serve a variety of functions as carriers, vehicles, diluents, binders, preservatives, buffers, pH adjusters, emulsifiers, and other formulating aids.

The compositions of the present invention also include dosage form comprising solutions and suspensions prepared for use for application to the buccal mucosa to provide immediate therapeutic levels of the formulation.

The buccal mucosa dosage form of the invention will optionally include one or more suitable and pharmaceutically acceptable inactive excipients, including but not limited to, preservatives, buffers, vehicles, and pH adjusters as recited above with respect to "eye drop" dosage forms. As noted, the above inactive excipients serve a variety of functions as carriers, vehicles, diluents, binders, preservatives, buffers, pH adjusters, emulsifiers, and other formulating aids.

The compositions of the present invention also include dosage forms for use in the topical treatment of cutaneous manifestations of HSV infections prepared in a variety of forms including ointments, gels, and creams. These preparations optionally include one or more of the following suitable and pharmaceutically acceptable excipients: isopropyl myristate NF, trolamine NF, SD alcohol 40 (20%), white petrolatum USP, lanolin alcohols NF, mineral oil USP, polyvinyl alcohol gel, cetostearyl alcohol NF, lactic acid USP, calcium stearate, dextran, polyoxyl 40 stearate, methylparaben, propylene glycol, sodium lauryl sulfate, polyethylene glycol (PEG) base, synthetic beeswax (B wax), calcium acetate, purified water USP and similar products. The above excipients serve a variety of functions as carriers, vehicles, diluents, binders, preservatives, buffers, pH adjusters, emulsifiers, and other formulating aids.

The compositions of the present invention also include dosage forms for local use in treating female genital manifestations of HSV infections, especially HSV-2, are prepared in dosage forms for vaginal insertion including vaginal suppositories, gels, and tablets. These preparations optionally can include one or more of the following suitable and pharmaceutically acceptable excipients, including but not limited to: isopropyl myristate NF, mineral oil USP, stearyl alcohol NF, benzoic acid USP, pegoxyl 7 stearate, methylparaben, propylparaben, propylene glycol, butylated hydroxyanisole, coconut or palm kernel oil triglycerides, polysorbate 60 or polysorbate 8, peglicol 5, PEG-100 stearate and sorbitan monostearate, calcium lactate, hydroxypropyl methylcellulose, polysaccharide carrageenan corn starch, lactose, calcium lactate, silicon dioxide and purified water USP, among others. The above excipients serve a variety of functions as carriers, vehicles, diluents, binders, preservatives, buffers, pH adjusters, emulsifiers, and other formulating aids.

For intravenous administration, the dosage of the immunoglobulin compositions of the invention and the method of administration will vary with the severity and nature of the particular condition being treated, the duration of treatment, the adjunct therapy used, the age and physical condition of the subject of treatment. However, single dosages for intravenous administration can typically range from about 50 mg to about 10 g per kilogram body weight, or from about 100 mg to about 5 g per kilogram of body weight (unless otherwise indicated, the unit designated "mg/kg" or "g/kg", as used herein, refers to milligrams or grams per kilogram of body weight).

EXAMPLES

Example 1

Growth of HSV and Preparation of Virus Stocks

Herpes simplex virus (HSV-1 Walki) was routinely propagated on African green monkey kidney cells (Vero cells; ATCC CCL-81); however, many tissues-culture lines can be used for the growth and quantification of HSV (Herpes Simplex Virus Protocols, 1998, Ed. S. M. Brown & A. R. MacLean, Humana Press, Totowa, N.J.). The Vero cells were grown in M199 media supplemented with 5% fetal calf serum (FCS), 2 mM glutamine, 100 IU/ml penicillin, 100 $\mu$g/ml streptomycin in cell culture flasks (e.g. 175 $cm^2$/25-50 ml) at 37° C. in the presence of 5% $CO_2$. Cells were split 1:4 twice a week (cell viability >95%). For virus infection, the medium was removed, the cells were washed with Hank's solution, trypsinized with 0.05% trypsin, 0.02% EDTA (Seromed, L2143), seeded at a density of 4×10$^5$ cells per ml in cell culture flasks, and incubated for 24 hours at 37° C. in the presence of 5% $CO_2$. The medium was removed and virus suspension was added at a multiplicity of infection (m.o.i) of <0.05 in a volume of 2 ml per 175 $cm^2$ surface area. The flask was allowed to stand 1 hour at 37° C. in the presence of 5% $CO_2$ with occasional agitation to distribute the virus evenly over the cells. Then medium was added to a final volume of 50 ml per 175 $cm^2$ tissue culture flask. The cultures were incubated until all cells showed signs of infection (approximately 2–3 days). To harvest the virus, flasks were frozen at −80° C. and thawed at 37° C. (in a water bath) two times. Cell debris was removed by centrifugation (300 g, 10 min, 4° C.) and the supernatant was stored in aliquots at −80° C.

The titer of the virus stock was determined in a plaque assay. Briefly, Vero cells were seeded at a density of $4 \times 10^5$ cells per well of a 24-well tissue culture plate. After an incubation period of 24 hours (37° C., 5% $CO_2$) cells were infected with dilutions of the virus stock ranging from $10^{-2}$ to $10^{-8}$. Infection volume was 100 μl per well. After 1 hour incubation at 37° C., 5% $CO_2$ following infection, the cells were gently removed, covered with 1 ml overlay medium (0.5% methyl cellulose, 0.225% sodium bicarbonate, 2 mM glutamine, 100 IU/ml penicillin, 100 μg/ml streptomycin, 5% FCS in MEME (MEM-Eagle with Earle's salt)), and allowed to stand for 3 days at 37° C. in the presence of 5% $CO_2$. Cells were fixed with 4% formalin for at least 30 minutes, washed with water, stained with Giemsa solution (Merck, Darmstadt) for 30 minutes and washed again. After drying the plates, plaques were counted and the titer of the virus stock was calculated.

Example 2

Lethal Challenge Model

Balb/cABom female mice (weight 19 g, age 7 weeks) were purchased (M&B A/S, Denmark) and inoculated 1 week later. 50 μl of a diluted virus suspension (HSV-1 Walki) in ice-cold PBS (~$5 \times 10^4$ pfu) was applied to the nares of lightly ether-anesthetized mice, resulting in a mortality of 90–100% after 7–10 days. Infected animals were inspected daily for signs of disease (encephalitis, paralysis, respiratory symptoms) and moribund animals were euthanized.

Example 3

Ocular Herpes Model

Balb/cABom female mice (weight 19 g, age 7 weeks) were purchased (M&B A/S, Denmark) and inoculated 1 week later. Mice were anesthetized by ether and the right cornea was scratched three times vertically and three times horizontally with a sterile 30-gauge needle. 5 μl of virus suspension ($5 \times 10^6$ pfu HSV-1 Walki) was applied to the scarified cornea. Mice were inspected daily for signs of herpes infection (blepharitis, keratitis, encephalitis). Moribund animals were euthanised.

Example 4

Immunoglobulin Fractions

Human immunoglobulin fractions, IgG, monomeric IgA (mIgA), and dimeric IgA (dIgA), were prepared as follows.

IgG used in the examples was commercial grade IgG (5% GAMIMMUNE N, Bayer Corp., Pittsburgh, Pa.) purified from pooled human plasma using Cohn fraction II+III as starting material. Monomeric IgA and dIgA from human plasma were purified by two consecutive size-exclusion chromatography steps on SUPERDEX 200 using a BIO-LOGIC chromatography station (Bio Rad, Richmond, Calif.). The high-salt strip of the Q-SEPHAROSE chromatography step, a waste stream of the IGIV-C process (see U.S. Pat. No. 6,307,028, fully incorporated herein by reference), was used as starting material and contained 13 mg/ml of IgA at a purity of 45%.

Figure 1A:
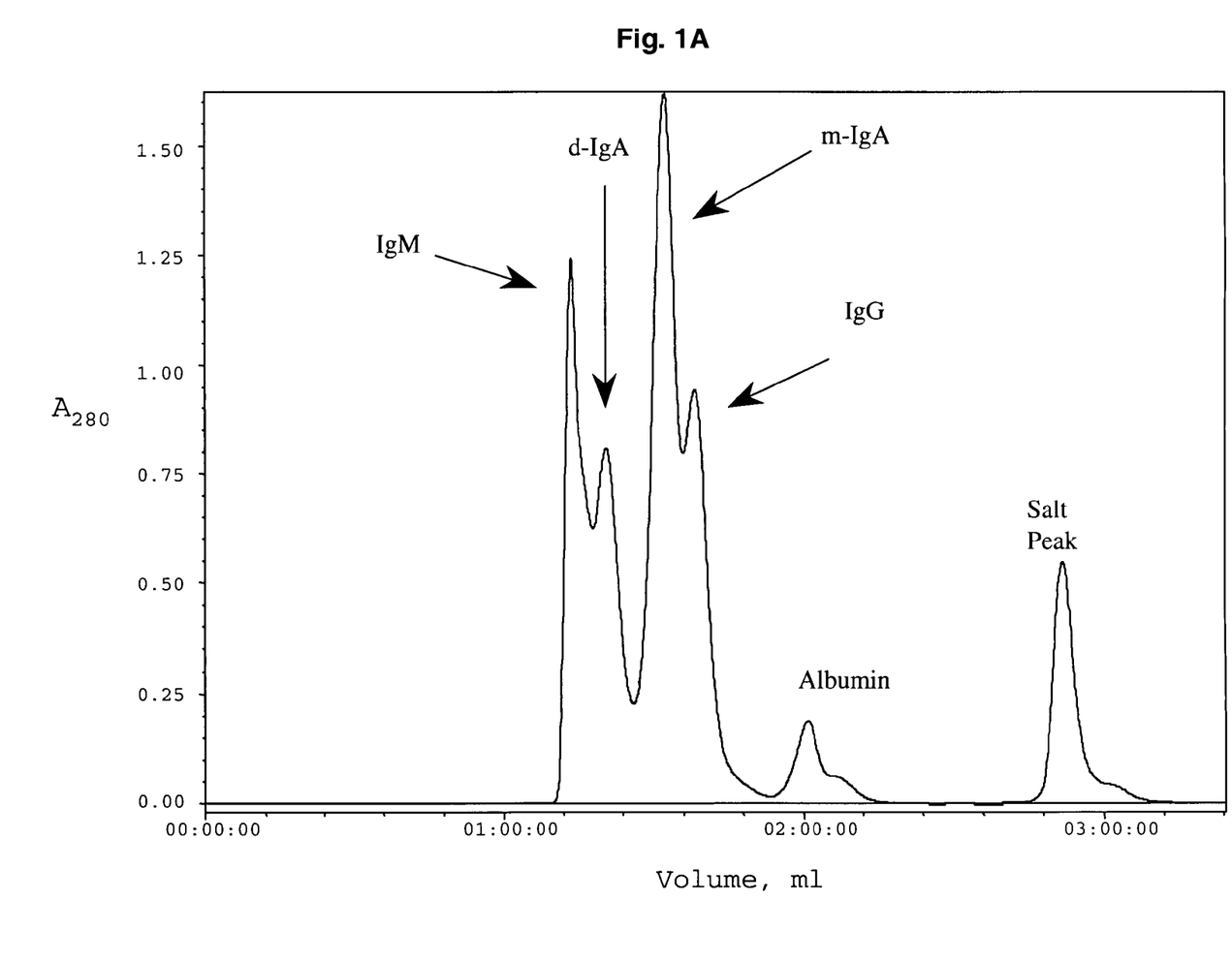
FIGS. 1A and 1B show graphic representations of elution profiles of immunoglobulin from first and second size exclusion (gel filtration) chromatographic columns, respectively.
Figure 1B:
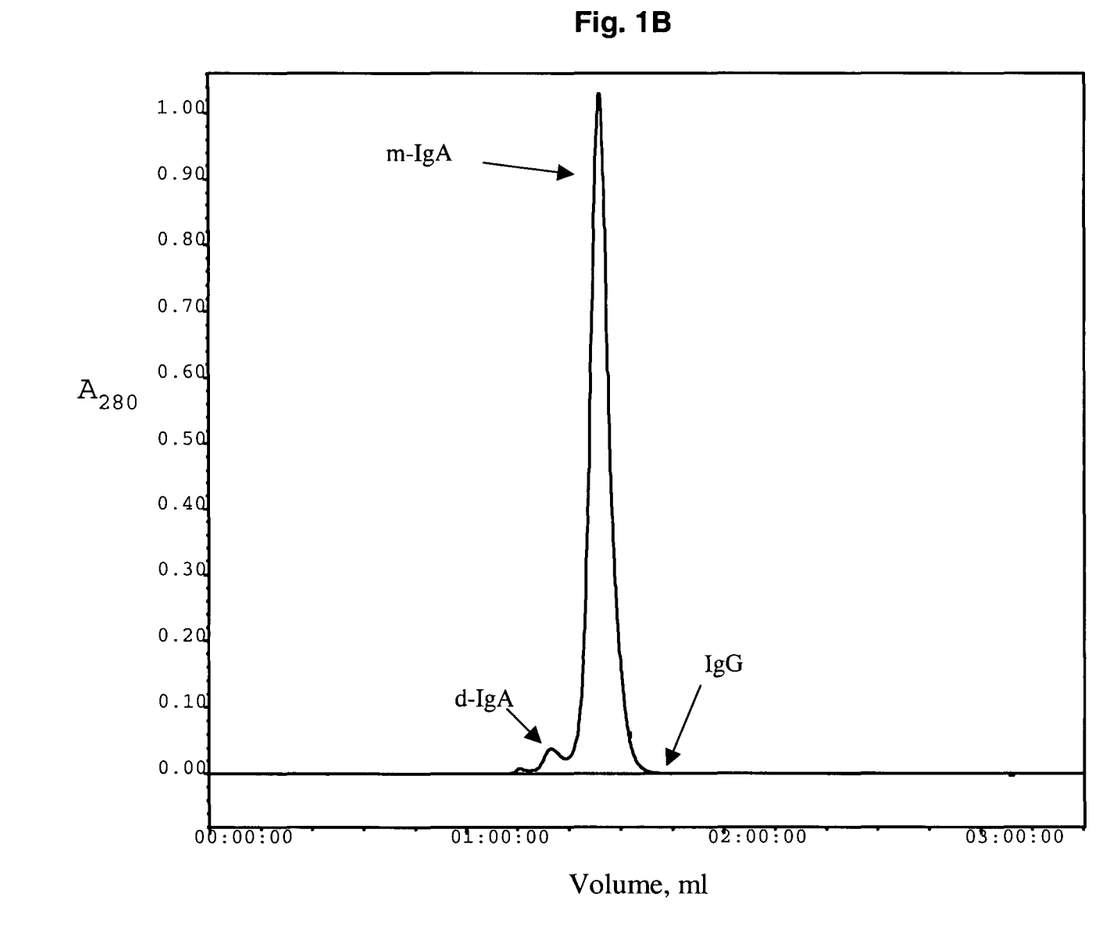
Figure 2:
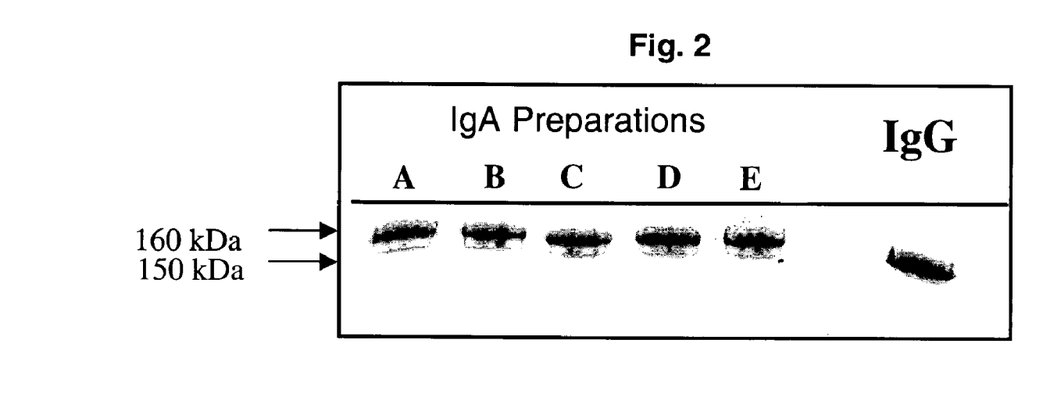
FIG. 2 shows SDS-PAGE of purified IgA (after a second size exclusion chromatographic purification step), migrating as a major band at 160 kDa with a minor band at 150 kDa.
Figure 3A:
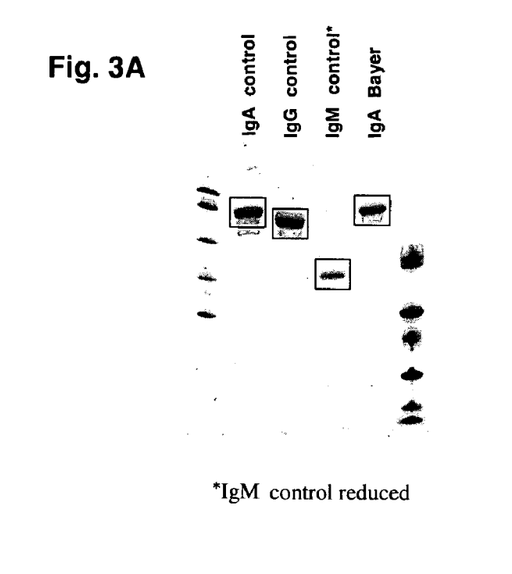
FIGS. 3A and 3B show non-reduced SDS-PAGE and a western blot, respectively, of an IgA preparation of the invention (after second size exclusion chromatographic purification).
Figure 3B:
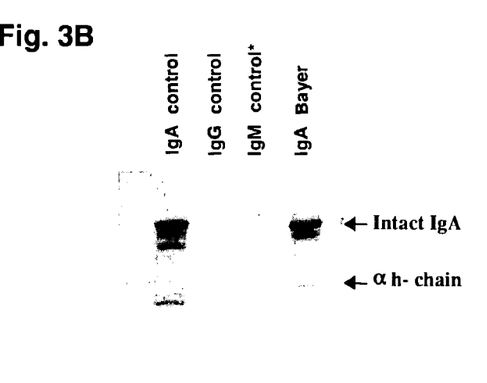
Figure 4A:
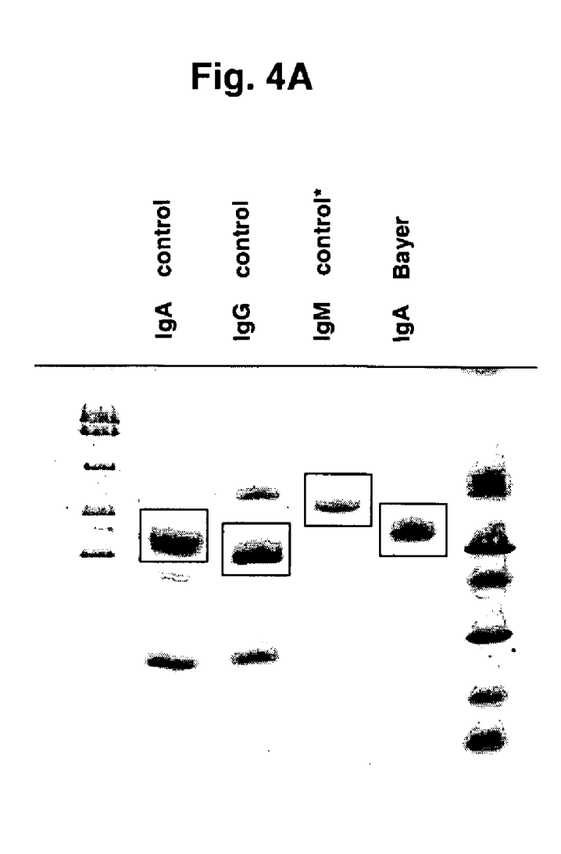
FIGS. 4A and 4B show reduced SDS-PAGE and a western blot, respectively, corresponding to the analysis under non-reducing conditions as presented in FIGS. 3A and 3B.
Figure 4B:
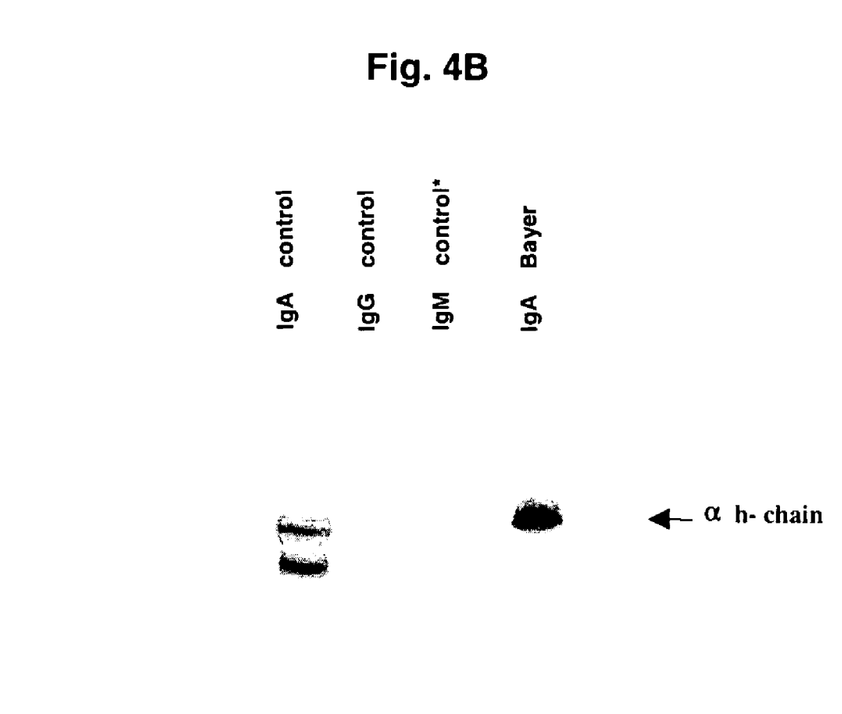

Briefly, 20 ml of starting material were applied to a 2-liter 200 XK 50/100 SUPERDEX 200 column (5 cm×93 cm, Pharmacia, Upsala, Sweden) and run at 10 ml/min in Tris Buffered Saline buffer (Sigma, St. Louis, Mo.). Fractions were analyzed by nephelometry, SDS-PAGE, and size exclusion-FPLC. Fractions positive for monomeric IgA were pooled, concentrated to a final volume of 10 ml with an AMICON concentration chamber (YM 10 membrane, RT), and reapplied to the SUPERDEX 200 column using the same running conditions as in the first run. The final product was formulated in 0.2 M glycine, pH 4.25 and sterile filtered using a 0.2 μm membrane. The elution profile (280 nm) of the first chromatography had five protein peaks, which were identified by immunonephelometry as IgM, dIgA, mIgA, IgG and albumin (see FIG. 1A). Re-chromatography of the mIgA and the dIgA peak on SUPERDEX 200 resulted in one major protein peak and two small shoulders, which contained mIgA, dIgA and IgG, respectively (see FIG. 1B). Fractions containing mIgA or dIgA were pooled. The identity of IgA was further confirmed by SDS-PAGE and western blots (see FIGS. 2, 3A, 3B, 4A, and 4B). Aliquots were stored frozen at −70° C.

Example 5

Human IgG for the Prevention/Treatment of Ocular HSV-Disease

For the ocular herpes model, immunoglobulin suspensions were diluted in PBS prior to the treatment of infected animals to a final concentration of 25 mg/ml. Mice were treated topically by applying 5 μl of the diluted immunoglobulin suspension directly on the infected eye's cornea 3 times daily. On the day of infection treatment was given 1 hour prior to infection, 1 hour post-infection (p.i.) and 5 hours p.i. From day 1 p.i. to day 4 p.i., animals were treated 3 times daily at 7 a.m., 2 p.m. and 7 p.m.

Mice were infected with HSV on the cornea of one eye and treated on the day of infection and on the 4 following days 3 times per day with human IgG, mIgA and dIgA as described above, or with placebo (phosphate buffered saline, PBS=150 mM NaCl, 20 mM phosphate, pH 7.0–7.4). At day 7 post infection, out of a total of 10 infected mice receiving each treatment, the following number survived:

TABLE 1

| | # Survivors |
|---|---|
| Placebo | 0 |
| IgG | 7 |
| mIgA | 0 |
| dIgA | 1 |

Seven days after infection, all animals treated only with placebo had developed ocular HSV disease in combination with a lethal HSV encephalitis, while 7 out of 10 animals treated with topical IgG 3 times per day had survived and showed no signs of ocular HSV-disease.

Example 6

Human dIgA for Prevention/Treatment of Disseminated HSV Disease

In the lethal challenge model, animals were treated by injection of the immunoglobulin suspension into the tail vein. Treatment was given 1 hour prior to infection and 24 hour p.i. On the day of infection, 2 mg of immunoglobulin were applied; on the day after infection another 2 mg were given.

Mice were infected with HSV intranasally and treated on the day of infection and the day after infection by intravenous injection of IgG, mIgA, dIgA or placebo (phosphate buffered saline, PBS). At day 7 post infection, out of a total of 10 infected mice, the following number survived:

TABLE 2

|         | # Survivors |
|---------|-------------|
| Placebo | 0           |
| IgG     | 9           |
| mIgA    | 5           |
| dIgA    | 7           |

Seven days after infection, all placebo-treated animals had succumbed to a lethal disseminated HSV-infection, while 7 out of 10 animals treated with intravenous dIgA, and 5 out of 10 animals treated with intravenous mIgA, survived.

The foregoing Examples of the invention are illustrative only, and are not intended to be limiting of the invention in any way. Those of skill in the art will recognize that various modifications of the foregoing are within the intended scope of the invention.

What is claimed is:

1. A method of treatment of herpes simplex virus (HSV) infections in mammals, the method comprising, administering intravenously to a mammal an effective amount of a composition comprising monomeric IgA, dimeric IgA, and IgG prepared from pooled human plasma, wherein monomeric and dimeric IgA comprise at least from about 35% to about 55% of the total immunoglobulins present in the composition.

2. The method of claim 1, wherein monomeric and dimeric IgA comprise at least from about 60% to about 80% of the total immunoglobulins present in the composition.

3. The method of claim 1, wherein monomeric and dimeric IgA comprise at least from about 70% to about 95% of the total immunoglobulins present in the composition.

4. The method of claim 1, wherein monomeric and dimeric IgA comprise at least about 60% of the total immunoglobulins present in the composition.

5. The method of claim 1, wherein monomeric and dimeric IgA comprise at least about 80% of the total immunoglobulins present in the composition.

6. The method of claim 1, wherein monomeric and dimeric IgA comprise at least 90% of the total immunoglobulins present in the composition.

* * * * *

UNITED STATES PATENT AND TRADEMARK OFFICE
CERTIFICATE OF CORRECTION

PATENT NO.       : 6,984,492 B2  
APPLICATION NO. : 10/656781  
DATED            : January 10, 2006  
INVENTOR(S)      : Betz et al.

Page 1 of 1

It is certified that error appears in the above-identified patent and that said Letters Patent is hereby corrected as shown below:

At Item [56] the following cited reference was omitted from the U.S. Patent Documents Section:

U.S. Pat. No. 6,307,028 B1, 10/2001, Lebing, *et al.*, 530/390.1

Signed and Sealed this

Twelfth Day of December, 2006

JON W. DUDAS  
*Director of the United States Patent and Trademark Office*